Figure 1:
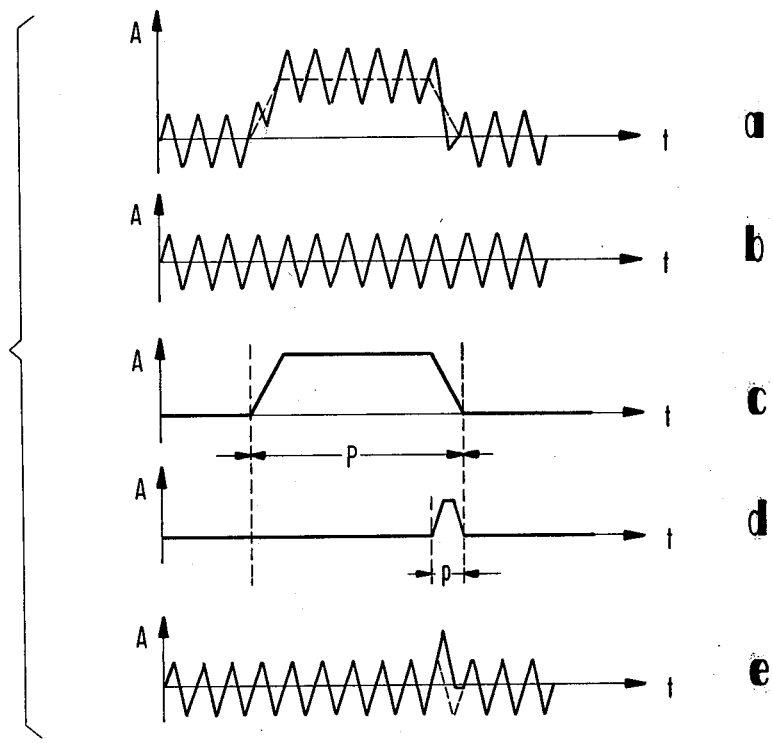

United States Patent [19]

Huber et al.

[11] 4,182,190
[45] Jan. 8, 1980

[54] METHOD FOR SIMULATING DYNAMIC LOADS AND APPARATUS FOR CARRYING OUT THE METHOD

[75] Inventors: Guntram Huber, Aidlingen-Dachtel; Walter Schmid, Sindelfingen, both of Fed. Rep. of Germany

[73] Assignee: Daimler-Benz Aktiengesellschaft, Fed. Rep. of Germany

[21] Appl. No.: 922,679

[22] Filed: Jul. 7, 1978

[30] Foreign Application Priority Data

Jul. 8, 1977 [DE] Fed. Rep. of Germany ....... 2730914

[51] Int. Cl.² .............................................. G01N 3/32
[52] U.S. Cl. ........................................ 73/794; 73/669
[58] Field of Search ............... 73/794, 795, 796, 797, 73/798, 12, 669, 670

[56] References Cited

U.S. PATENT DOCUMENTS

| | | | |
|---|---|---|---|
| 3,664,179 | 5/1972 | Danko et al. | 73/797 X |
| 3,712,125 | 1/1973 | Meyer | 73/794 X |

*Primary Examiner*—Jerry W. Myracle
*Attorney, Agent, or Firm*—Craig and Antonelli

[57] ABSTRACT

A method and apparatus for simulating dynamic loads in structural parts, especially in motor vehicle bodies, with an introduction of tensional compressive and torsional forces longitudinally, transversely, and vertically to the driving direction; at least for one introduced force, the low frequency component of the signal is separated off, is transformed sectionwise to higher frequencies and is then added, shifted with respect to time, to the structural part to be loaded.

9 Claims, 2 Drawing Figures

METHOD FOR SIMULATING DYNAMIC LOADS AND APPARATUS FOR CARRYING OUT THE METHOD

The present invention relates to a method for the simulation of dynamic loads in structural parts, especially in motor vehicle bodies, with introduction of tensional-, compressive- and/or torsional forces longitudinally, transversely, and/or vertically with respect to the driving direction, and to an apparatus for carrying out this method.

For example, for the simulation of a poor-road, endurance test of a vehicle on a test stand, the actual load of the wheels, axles, body, etc. during a drive on a test track or test section is measured, and the corresponding signals are stored, for example, on a magnetic tape. On the test stand, these signals are again converted into movements, which are intended to load or stress the vehicle as identically as possible as during the drive. Dynamic forces, which act on the vehicle transversely or vertically to the driving direction—by way of the wheels thereof respectively the wheel hubs thereof—can be simulated without difficulty. Quasi-static forces, in contrast thereto, which act over a relatively long period of time, for example, without polarity change, for example, travels or displacements which result during the simulation of superimposed braking operations with a realistic representation of the load or stress longitudinally of the driving direction, however, are not available, at the test stand. In the case of a vehicle a remedy would be possible if either the vehicle body were held fast—this however would produce loads and stresses at places which do not occur or occur differently during the drive on the test track, i.e., falsifications—or if the vehicle were correspondingly accelerated or decelerated over longer distances, which is equally not possible on the limited test stand.

It is the aim of the present invention to so improve the known method for the simulation of dynamic loads that also static forces are adapted to be fed and applied to the structural parts on the test stand. Additionally, it is an aim of the present invention to provide an installation for carrying out this method.

The underlying problems are solved according to the present invention in that for at least one introduced force, the low frequency component of the signal is separated off, is transformed sectionwise to higher frequencies and is supplied, shifted with respect to time, to the structural part to be loaded.

Since travels or displacements during an oscillating load with a given acceleration, from which result the load forces, are inversely proportional to the square of the frequency, a comparable load of the vehicle structure with acceptable small displacements can be simulated in this manner. Attention has to be paid only to the fact that resonance appearances are not unnaturally strongly over-emphasized or de-emphasized, in that for example, the high transformed-up frequencies still remain below the lowest resonant frequency of the structural part to be examined. Higher frequency load components are designated as "dynamic forces" and lower frequency components as "static forces."

In a preferred method according to the present invention, provision is made that the timing periods, i.e., the duration of the transformation section is constant. This enables a somewhat more simple construction of the test installation. However, it is also possible to keep the timing period variable, for example, in order to avoid at large loads the continuous reaching of the end points of the adjusting members by a different frequency ratio.

An increase of the frequency also requires a compression and therewith a time displacement of the force engagement duration. In a preferred manner of operation of the method according to the present invention, the time displacement takes place in such a manner that the transformation section, respectively, the timing period and the time displacement terminate at the same time.

An installation according to the present invention for carrying out the method is so constructed that for each force introduced in a direction, a high-pass filter and parallel thereto a low-pass filter with a transformation element are provided, that furthermore a summing or adding element with one inverting and two non-inverting inputs is provided, whereby the output of the high-pass filter is connected with the one non-inverting input and the output of the transformation element is connected alternately with the other non-inverting or the inverting input, and the output of the summing element leads by way of an amplifier to the adjusting member. As a rule, a computer installation of a conventional construction is interconnected as transformtion element which is connected in the output of the low-pass filter and is either connected ahead of the summing element during direct operation or computes a signal with the use of the signals of the dynamically acting forces and stores the same on a tape which corresponds to the signal appearing at the output of the summing element in direct operation. With both types of operation, provision is made that the signal component at the output of the transformation element is reversed in polarity if the adjusting member arrives at one or the other end point of its travel range; in one case by direct feedback of the end position and in the other case by precalculation of the reaction of the adjusting member on the contol signals.

Accordingly, it is an object of the present invention to provide a method and apparatus for the simulation of dynamic loads in structural parts, especially in motor vehicle bodies, which avoid by simple means the aforementioned shortcomings and drawbacks encountered in the prior art.

Another object of the present invention resides in a method and apparatus for simulating dynamic loads in structural parts which permit the simulation of both dynamic as well as static loads without falsification of the results.

A further object of the present invention resides in a method for simulating dynamic loads in structural parts which assures highly accurate results notwithstanding complex, superimposed force interactions.

Figure 2:
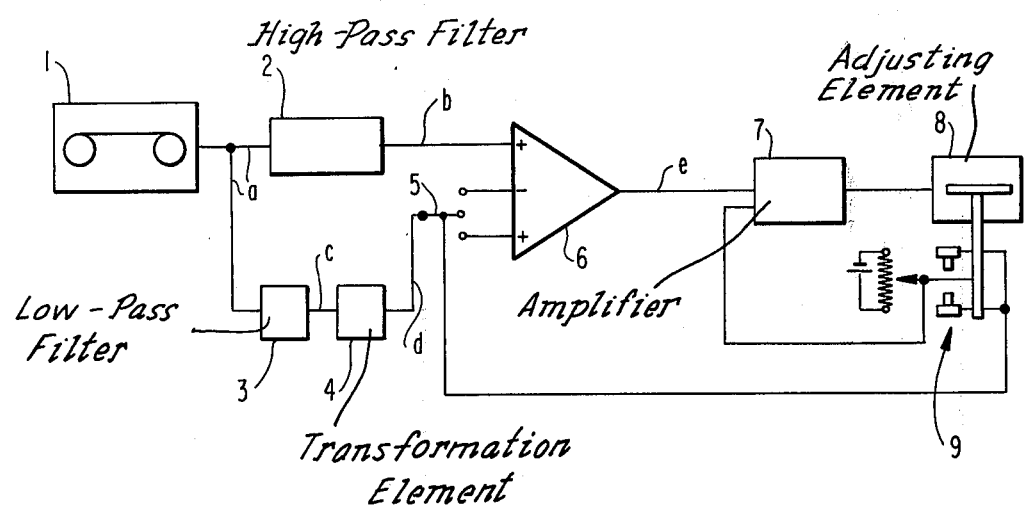

These and other objects, features and advantages of the present invention will become more apparent from the following description when taken in connection with the accompanying drawing which shows, for purposes of illustration only, one embodiment in accordance with the present invention, and wherein:

FIGS. 1a through 1e are diagrams illustrating the individual steps of the method according to the present invention, and FIG. 2 is an installation for carrying out the method in accordance with the present invention.

Referring now to FIG. 1 of the drawing, the method of the present invention is illustrated in detail in the various wave diagrams thereof. Assumed is thereby a force acting on a wheel hub longitudinally of the driving direction. The signal of the amplitude over a period of time during a braking operation which is measured on the road-test section and which is stored on the tape is schematically illustrated in the diagram a.

The high frequency oscillations are assumed as triangular voltage of constant frequencies, superimposed by a low-frequency trapezoidally shaped voltage caused by the braking action, which is illustrated in dash line. This signal is split up by way of a filter into a high frequency component (diagram b) and into a low-frequency component (diagram c). The low-frequency component is now periodically transformed with the aid of the transformation element—of an electronic computer installation—to a higher frequency at a predetermined ratio. In FIG. 1, the signal with the period or duration P (diagram c) is "compressed" approximately to ten times the frequency having the duration p (diagram d) and the amplitude A is determined corresponding to the already mentioned inter-relation between displacement and frequency (diagram d) and this signal is added to the high frequency component according to diagram b (diagram e). This signal (diagram e) is fed to the adjusting member—either directly or stored on tape. During the period the low frequency signal may also be integrated and the adjusting member may be brought into a corresponding preparatory or lead position, from which the transformed signal is fed subsequently "bunched together."

FIG. 2 illustrates schematically an installation for the described method. The signal which had been recorded on tape during the drive on the test section (diagram of FIG. 1) is reproduced by way of a tape recorder apparatus 1 and is simultaneously fed to a high-pass filter 2 and to a low-pass filter 3. The transformation element 4, the electronic computer installation, is connected to the output of the low-pas filter 3. The signal c (of the diagram c) is "compressed" in the transformation element 4 into signal d (of diagram d) and is fed during direct operation with the computer installation to a reversing switch 5 which, depending on the position of the adjusting member 8, feeds the same to an interverting or to a non-inverting input of a summing or adding element 6. The signal b (diagram b) coming from the high-pass filter 2 is fed to a further non-inverting input of the summing or adding element 6. Both signals are added in the summing element 6, and the signal e (diagram e) resulting therefrom is amplified in an amplifier 7 and is fed to the adjusting element 8. The end positions of the adjusting element 8 are detected by electric contacts 9 which bring the reversing switch 5 into the respectively other position as long as the adjusting member 8 remains in this end position. Since the electrical and electronic devices and circuits involved in the elements depicted in block diagram are known as such in the art, a detailed description thereof is dispensed with herein for the sake of clarity.

Such an installation is provided for each force direction.

While we have shown and described only one embodiment in accordance with the present invention, it is understood that the same is not limited thereto but is susceptible of numerous changes and modifications as known to those skilled in the art, and we therefore do not wish to be limited to the details shown and described herein but intend to cover all such changes and modifications as are encompassed by the scope of the appended claims.

We claim:

1. A method for simulating dynamic loads in structural parts of a vehicle with introduction of tensional, compressive, and torsional forces longitudinally, transversely, and vertically to a driving direction of the vehicle, comprising the steps of separating at least for one of the introduced forces a low-frequency component of the signal, transforming the thus separated component sectionwise to higher frequencies, and feeding the thus-transformed signal, displaced with respect to time, to the structural part to be loaded.

2. A method according to claim 1, characterized in that the transforming of the component sectionwise to higher frequencies is effected over a timing period having an essentially constant duration.

3. A method according to claim 1 or 2, characterized in that the transforming of the component sectionwise to higher frequencies is effected over a timing period having an essentially variable duration.

4. A method according to claim 1, characterized in that the displacement with respect to time takes place in such a manner that the transforming of the component sectionwise to higher frequencies and the displacement with respect to time terminate substantially at the same time.

5. A method according to claim 4, characterized in that the transforming of the component sectionwise to higher frequencies is effected over a timing period having an essentially constant duration.

6. A method according to claim 4, characterized in that the transforming of the component sectionwise to higher frequencies is effected over a timing period having an essentially variable duration.

7. An installation for simulating dynamic loads in structural vehicle parts with an introduction of tensional, compressive, and torsional forces, longitudinally, transversely, and vertically to a driving direction of the vehicle, characterized in that a high-pass filter means and a low-pass filter means in parallel to the high-pass filter means are provided for a force introduced in a given direction, a transformation means operatively connected to the output of the low-pass filter means, an adding element having one inverting and two non-inverting inputs, the output of the high-pass filter means being operatively connected with one non-inverting input and the output of the transformation means being operatively connected alternately with the other non-inverting input or with the inverting input of the adding element, and the output of the adding element being fed by way of an amplifier to an adjusting means.

8. An installation according to claim 7, characterized in that a signal component at the output of the transformation means is reversed in polarity if the adjusing means arrives at one or the other end point of its travel range.

9. An installation according to claims 7 or 8, characterized in that a high-pass filter means and low-pass filter means with transformation means, as well as an adding element operatively connected to an adjusting means, is provided for each introduced force.

* * * * *